US007565197B2

(12) United States Patent
Haubrich et al.

(10) Patent No.: US 7,565,197 B2
(45) Date of Patent: Jul. 21, 2009

(54) CONDITIONAL REQUIREMENTS FOR REMOTE MEDICAL DEVICE PROGRAMMING

(75) Inventors: Gregory J. Haubrich, Champlin, MN (US); David S. Jennings, Minneapolis, MN (US); Christopher M. Petersen, Ham Lake, MN (US); Javaid Masoud, Shoreview, MN (US); John P. Vandanacker, Greenfield, MN (US); James E. Willenbring, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 831 days.

(21) Appl. No.: 10/871,591

(22) Filed: Jun. 18, 2004

(65) Prior Publication Data

US 2005/0283198 A1 Dec. 22, 2005

(51) Int. Cl.
*A61N 1/00* (2006.01)
(52) U.S. Cl. ...................................... 607/30
(58) Field of Classification Search ............. 607/30, 607/32, 60, 31; 128/903, 904
See application file for complete search history.

(56) References Cited

U.S. PATENT DOCUMENTS

| | | | |
|---|---|---|---|
| 5,312,453 A | 5/1994 | Shelton et al. | |
| 5,345,362 A | 9/1994 | Winkler | |
| 5,456,692 A * | 10/1995 | Smith et al. | 607/31 |
| 5,545,186 A | 8/1996 | Olson et al. | |
| 5,987,352 A | 11/1999 | Klein et al. | |
| 6,073,049 A * | 6/2000 | Alt et al. | 607/31 |
| 6,169,925 B1 | 1/2001 | Villaseca et al. | |
| 6,240,317 B1 | 5/2001 | Villaseca et al. | |
| 6,249,703 B1 | 6/2001 | Stanton et al. | |
| 6,363,282 B1 | 3/2002 | Nichols et al. | |
| 6,385,593 B2 | 5/2002 | Linberg | |
| 6,418,346 B1 | 7/2002 | Nelson et al. | |
| 6,438,408 B1 | 8/2002 | Mulligan et al. | |
| 6,442,433 B1 * | 8/2002 | Linberg | 607/60 |
| 6,471,645 B1 | 10/2002 | Warkentin et al. | |
| 6,482,154 B1 * | 11/2002 | Haubrich et al. | 607/32 |
| 6,493,587 B1 * | 12/2002 | Eckmiller et al. | 607/31 |
| 6,497,655 B1 | 12/2002 | Linberg et al. | |

(Continued)

FOREIGN PATENT DOCUMENTS

WO W00147599 A 7/2001

OTHER PUBLICATIONS

International Search Report, PCT/US2005/021897, May 7, 2006, 5 Pages.

*Primary Examiner*—Mark W Bockelman
*Assistant Examiner*—Roland Dinga

(57) ABSTRACT

A remote programming method is provided for safe and secure programming of a medical device at a remote location. A centralized programming instrument for use by a clinician or third party is provided with a network communication connection with a remote external medical device, such as a home programmer or monitor. The external medical device is located in the vicinity of a patient having an implantable medical device (IMD) and is in bi-directional telemetric communication with the IMD to allow instructions received from the centralized programming instrument to be transferred to the IMD. The remote programming method used for transferring information between the central programming instrument and an IMD includes measures to promote safe and secure remote programming of the IMD, which measures may include authorization requirements, programming condition requirements, implementation of programmed data requirements, and maintenance of a remote programming log.

32 Claims, 9 Drawing Sheets

U.S. PATENT DOCUMENTS

| | | |
|---|---|---|
| 6,561,975 B1 | 5/2003 | Pool et al. |
| 6,564,104 B2 | 5/2003 | Nelson et al. |
| 6,574,511 B2 | 6/2003 | Lee |
| 6,622,045 B2 | 9/2003 | Snell et al. |
| 6,647,299 B2 | 11/2003 | Bourget |
| 2001/0031071 A1* | 10/2001 | Nichols et al. ............... 382/115 |
| 2001/0039504 A1* | 11/2001 | Linberg et al. ................. 705/3 |
| 2002/0040234 A1* | 4/2002 | Linberg ....................... 607/32 |
| 2002/0143372 A1* | 10/2002 | Snell et al. .................... 607/30 |
| 2003/0041866 A1* | 3/2003 | Linberg et al. .............. 128/899 |

* cited by examiner

CONDITIONAL REQUIREMENTS FOR REMOTE MEDICAL DEVICE PROGRAMMING

FIELD OF THE INVENTION

The present invention relates generally to implantable medical device systems and more particularly to methods for remotely programming an implantable medical device (IMD).

BACKGROUND OF THE INVENTION

One goal of a technology-based health care system that fully integrates the technical and social aspects of patient care and therapy is to connect the client with care providers irrespective of separation distance or location of the participants. While clinicians will continue to treat patients in accordance with accepted medical practice, developments in communications technology are making it ever more possible to provide medical services in a time- and place-independent manner.

Past methods of clinical services are generally limited to in-hospital operations. For example, if a physician needs to review the performance parameters of an implantable device in a patient, the patient normally has to go to the clinic. Further, if the medical conditions of a patient with an implantable device warrant continuous monitoring or adjustment of the device, the patient would have to stay in a hospital indefinitely. Such a continued treatment plan poses both economic and social problems. Under the exemplary scenario, as the segment of the population with implanted medical devices increases many more hospitals/clinics and service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the past practice requires that a patient visit a clinical center for occasional retrieval of data from the implanted device to assess the operations of the device and gather patient history for both clinical and research purposes. Such data is acquired by having the patient in a hospital/clinic to download the stored data from the implantable medical device. Depending on the frequency of data collection, this procedure may pose a serious difficulty and inconvenience for patients who live in rural areas or have limited mobility. Similarly, in the event a need arises to upgrade the software of an implantable medical device, the patient will be required to come into the clinic or hospital to have the upgrade installed.

A further limitation of past practice relates to the management of multiple implantable devices in a single patient. Advances in patient therapy and treatment have made it possible to implant a number of devices in a patient. For example, implantable devices such as a defibrillator and/or a pacer, a neural implant, a drug pump, a separate physiologic monitor and various other implantable devices may be implanted in a single patient. To successfully manage the operations and assess the performance of each device in a patient with multiple implants requires a regular update and monitoring of the devices. Further, it may be preferred to have an operable communication between the various implants to provide a coordinated clinical therapy to the patient. Thus, there is a need to monitor the performance of the implantable devices on a regular, if not a continuous, basis to ensure optimal patient care. In the absence of other alternatives, this imposes a great burden on the patient if a hospital or clinic is the only center where the necessary frequent follow up, evaluation and adjustment of the medical devices could be made. Moreover, even if feasible, the situation would require the establishment of multiple service areas or clinic centers to provide adequate service to the burgeoning number of multi-implant patients worldwide. Accordingly, a programmer unit that would connect to a remote expert medical center to provide access to expert systems and import the expertise to a local environment is desirable. This approach would enable unencumbered access to the IMD or the patient.

To address these needs, a number of proposals have been made to enable remote programming and monitoring of an IMD from a centralized center. Using modern communications technologies, data may be transferred from a centralized programming instrument to a remote programming instrument located in the vicinity of a patient for transferring instructions received from the central location to the IMD. In U.S. Pat. No. 6,497,655 (Linberg et al.), a system is generally disclosed in which software programs are implemented in a web-enabled high-speed computer system to remotely monitor, manage and modify operation and functional parameters of a plurality of IMDs. In U.S. Pat. No. 6,442,433 (Linberg), a system for remote troubleshooting, maintenance and upgrade of implantable device systems is generally disclosed wherein a programmer operating in association with a diverse number of implantable medical devices is in bi-directional operable data, voice, and video communications with a remote web-based expert data center. In U.S. Pat. No. 6,363,282 (Nichols), a system and method for providing an automated software update to a programmer or equivalent device used in implantable medical device systems is generally disclosed. A system and method for providing automated self-identification information of a remote medical component of an implantable medical device system to a centralized computer is generally disclosed in U.S. patent application Pub. No. 2002/0040234 (Linberg). A system for transferring data into and out of medical devices wherein a personal data manager is used in a web-based network is generally disclosed in U.S. Pat. No. 6,418,346 (Nelson, et al.) A passive communication scheme between one or more external instruments communicable with one or more IMDs and with a remote central server or a network where data is stored is generally disclosed in U.S. Pat. No. 6,574,511 (Lee). A system and method for remote invoicing an inventory control of medical components of an implantable medical device system upon implantation in a patient is described in U.S. Pat. No. 6,385,593 (Linberg). All of the above patents are hereby incorporated herein by reference in their entirety.

The systems provide advantages with regard to remote patient management, but potential risks remain. Potential risks associated with remote IMD programming capabilities include inappropriate programming of an IMD or an adverse response to programming changes occurring when a patient is not under medical supervision. Furthermore, secure transfer of medical information across communication systems is important in protecting patient privacy.

BRIEF SUMMARY OF THE INVENTION

The present invention is directed toward providing a medical device system and method for remotely programming an IMD, which includes safety and security features for preventing unauthorized, unsecure, or unsafe programming of the IMD. A centralized programming instrument for use by a clinician or other medical personnel, also referred to herein generally as the "user," is provided with a communication network connection to enable bi-directional communication with a remote external medical device (EMD), such as a home programmer or monitor. The external medical device is located in the vicinity of a patient having an IMD and is in bi-directional telemetric communication with the IMD to allow instructions received from the centralized programming instrument to be transferred to the IMD. The remote programming method used for transferring information between the central programming instrument and an IMD includes measures to promote safe and secure remote programming of the IMD, which measures may include remote programming authorization requirements, programming condition requirements, implementation of programmed data requirements, and maintenance of a remote programming log.

In one embodiment, authorization requirements must be met before enabling remote programming to occur. Authorization requirements may include any of: user identification requirements that verify that the user and/or the central programming instrument being used are authorized to perform a remote programming operation; patient identification requirements that verify that the targeted patient and/or IMD are authorized to undergo remote programming and are correctly identified; and a third party authorization requirement that allows a third party other than the user and the patient to authorize an intended remote programming operation. Authorization requirements may further include encryption/decryption or other transmission security methods that enable only authorized remote programming operations to occur and reduce the likelihood of unauthorized decryption of patient and programming data.

Remote programming methods may additionally or alternatively include programming condition requirements relating to the condition of the targeted patient or IMD at the time of remote programming. Such patient-related conditions may relate, for example, to: a temporal condition such as the time of day or time since implant; a physiological condition such as patient activity, posture, or current heart rhythm; patient logistical conditions such as the patient's location relative to emergency equipment or emergency responders, patient's notification of impending programming, or an established communication line between the patient and the user. Device-related programming condition requirements may include restrictions on the remote EMD type; the IMD type and its current operating or battery status; the telemetry method used for programming the IMD; the status of particular programmable parameters, ranges or limits; and the method used for activating the IMD to enable telemetric transmission of remote programming session data.

Remote programming methods may additionally or alternatively include implementation requirements that must be met before remotely programmed code or parameters are implemented by the IMD for controlling device operations. Such implementation requirements may include: verification of a complete transmission or remotely programmed instructions; confirmation by the user of programming changes reported by the IMD; a time delay before implementation takes place to allow cancellation of programmed changes; and verification of expected IMD status prior to implementation. When implementation requirements are unmet or results of a remote programming operation appear unacceptable, prior or default programming instructions may be restored.

Remote programming methods may additionally or alternatively include maintaining a log of remote programming sessions to allow audits or remote patient management to be performed. Upon completion of each remote programming session, session data may be stored in a log file, which may be located on the remote programming instrument, on a network server, on the associated EMD, or in the IMD. Stored session data may include date and time information, user identification, patient/device identification, original programmed settings, changed parameters, final programmed settings and other user-entered information.

The remote programming system and method provided by the present invention allows remote programming to be performed in a safe, secure manner by ensuring that only authorized programming operations occur under conditions appropriate for remote programming.

DETAILED DESCRIPTION OF THE PREFERRED EMBODIMENTS

Figure 1:
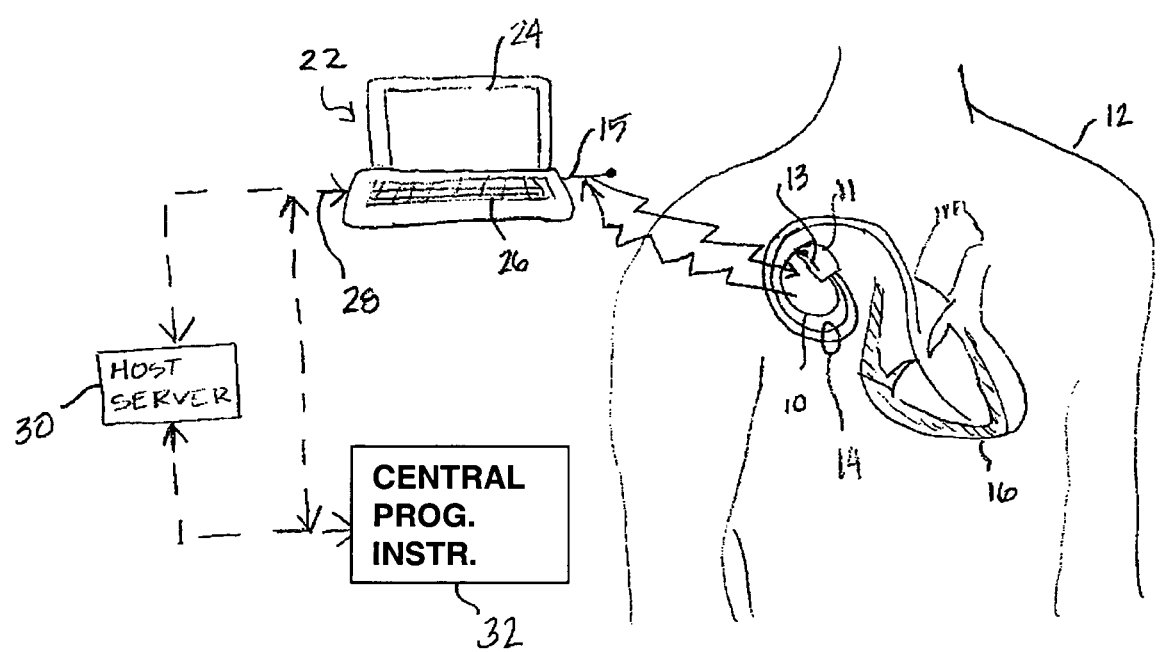
FIG. 1 is an illustration of a medical device system in which the present invention may be practiced.

As indicated above, the present invention includes a remote programming method for use with medical device systems that helps provide safe, secure programming of a medical device in a remote location. "Remote" programming, as used herein, refers to programming operations being performed when the patient having an IMD being programmed is not in the direct physical presence of a clinician or user performing the programming. FIG. 1 is an illustration of a medical device system in which the present invention may be practiced. The medical device system includes an IMD 10 and an EMD 22. IMD 10 is shown implanted in the body of a patient 12. The present invention may be implemented for use with a variety of programmable IMDs, including cardiac stimulation devices, cardiac or other physiological monitoring devices, neuromuscular stimulators, implantable drug pumps, or the like. For the sake of illustration, IMD 10 is shown here as a cardiac stimulation device coupled to a set of leads 14 used for positioning electrodes and optionally other physiological sensors in operative relation to the patient's heart 16. Leads 14 are coupled to IMD 10 via a connector block 11.

Examples of cardiac stimulation or monitoring devices with which the present invention may be employed are disclosed in U.S. Pat. No. 5,545,186 (Olson et al.), U.S. Pat. No. 5,987,352 (Klein et al.), and U.S. Pat. No. 6,438,408 (Mulligan et al.), all of which patents are incorporated herein by reference in their entirety.

IMD 10 is in telemetric communication with EMD 22 to allow data stored or being acquired by IMD 10 to be retrieved by EMD 22 during an interrogation or monitoring session. EMD 22 is also used to transfer code, operating parameters, or other instructions to IMD 10. Exemplary external devices that may be located in a patient's home having telemetric communication with an IMD are disclosed in U.S. Pat. No. 6,647,299 (Bourget), U.S. Pat. No. 6,564,104 (Nelson et al.), U.S. Pat. No. 6,561,975 (Pool et al.), U.S. Pat. No. 6,471,645 (Warkentin et al.) and U.S. Pat. No. 6,249,703 (Stanton et al.), all of which patents are incorporated herein by reference in their entirety.

Programming commands or data are transmitted between an IMD RF telemetry antenna 13 and an external RF telemetry antenna 15 associated with the external device 22. The external RF telemetry antenna 15 may be contained in a programmer RF head so that it can be located close to the patient's skin overlying the IMD 10. Such programmer RF heads are well known in the art. See for example U.S. Pat. No. 4,550,370 (Baker), incorporated herein by reference in its entirety. The external device 22 may be designed to universally program IMDs that employ conventional ferrite core, wire coil, RF telemetry antennas known in the prior art and therefore also have a conventional programmer RF head and associated software for selective use with such IMDs.

Alternatively, the external RF telemetry antenna 15 can be located on the case of the external device 22, and the external device 22 can be located some distance away from the patient 12. For example, RF telemetry antenna 15 may be integrated with external device 22 and external device 22 may be located a few meters or so away from the patient 12 and utilize long-range telemetry systems. Such long-range telemetry systems may be preferable over systems requiring an RF head such that passive telemetry transmission may occur between IMD 10 and external device 22 without patient interaction when IMD 10 is within a communication range of external device 22. Thus, patient 12 may be active, e.g., partaking in normal household activities or exercising during a telemetry transmission. Telemetry systems that do not require the use of a programmer RF head are generally disclosed in U.S. Pat. No. 6,240,317 (Villaseca et al.), U.S. Pat. No. 6,169,925 (Villaseca et al.), and U.S. Pat. No. 6,482,154 (Haubrich et al.), all of which patents are incorporated herein by reference in their entirety.

In an uplink telemetry transmission 17, the external RF telemetry antenna 15 operates as a telemetry receiver antenna, and the IMD RF telemetry antenna 13 operates as a telemetry transmitter antenna. Conversely, in a downlink telemetry transmission 19, the external RF telemetry antenna 15 operates as a telemetry transmitter antenna, and the IMD RF telemetry antenna 13 operates as a telemetry receiver antenna. Each RF telemetry antenna is coupled to a transceiver comprising a transmitter and a receiver. Any of a number of suitable programming and telemetry methodologies known in the art may be employed such as the RF encoded telemetry signal system generally disclosed in U.S. Pat. No. 5,312,453 (Wyborny et al.), incorporated herein by reference in its entirety.

External device 22 is shown in FIG. 1 to be embodied as a "programmer" used in conjunction with IMD 10. Programmers are well known in the art and generally include a display 24, user interface 26, and a control system typically in the form of one or more microprocessors in addition to the telemetry circuitry described above. However, the present invention is not limited to being practiced with an IMD system wherein the external device functions as an associated programmer or home monitor. The present invention may alternatively be practiced with an external medical device system wherein a bedside or portable device performs physiological monitoring or therapy delivery functions. For example, EMD 22 may alternatively be embodied as a bedside monitoring console that may include ECG monitoring, blood pressure monitoring, oxygen saturation monitoring, carbon dioxide monitoring, or other physiological signal monitoring. Whether EMD 22 is associated with an internal or external medical device system, EMD 22 is provided with a communication link 28 that allows external device 22 to receive information from and transfer information to a centralized programming instrument 32.

Centralized programming instrument 32 may be located at a clinical center or other patient management facility and be part of an expert system used for remotely managing IMDs. Centralized programming instrument 32 may be implemented on an Internet-enabled computer system or a computer system on a local area network (LAN), wide area network (WAN), telecommunications network, or the like, which allows communication link 28 to be established between central programming instrument 32 and EMD 22. Centralized programming instrument 32 may communicate with EMD 22 via a host server 30, which may be used to control remote programming protocols according to some embodiments of the present invention.

It is recognized that a remotely programmable medical device system and associated remote programming methods provided by the present invention may be embodied in a variety of systems, for example including multiple implantable devices, including various types of EMDs and telemetry systems used for communicating with the IMD(s), and various embodiments of a centralized programming instrument 32 and communication link 28. Centralized programming instrument 32, for example, may be a dedicated instrument or may represent programming functionality implemented in software on an existing computer system. Communication link 28 may be established via a modem connection or wireless communication technologies. Additional detailed descriptions of systems for remote management of implantable medical devices in which the present invention may be embodied are described in the previously incorporated references, such as the '433 patent to Linberg.

Figure 2:
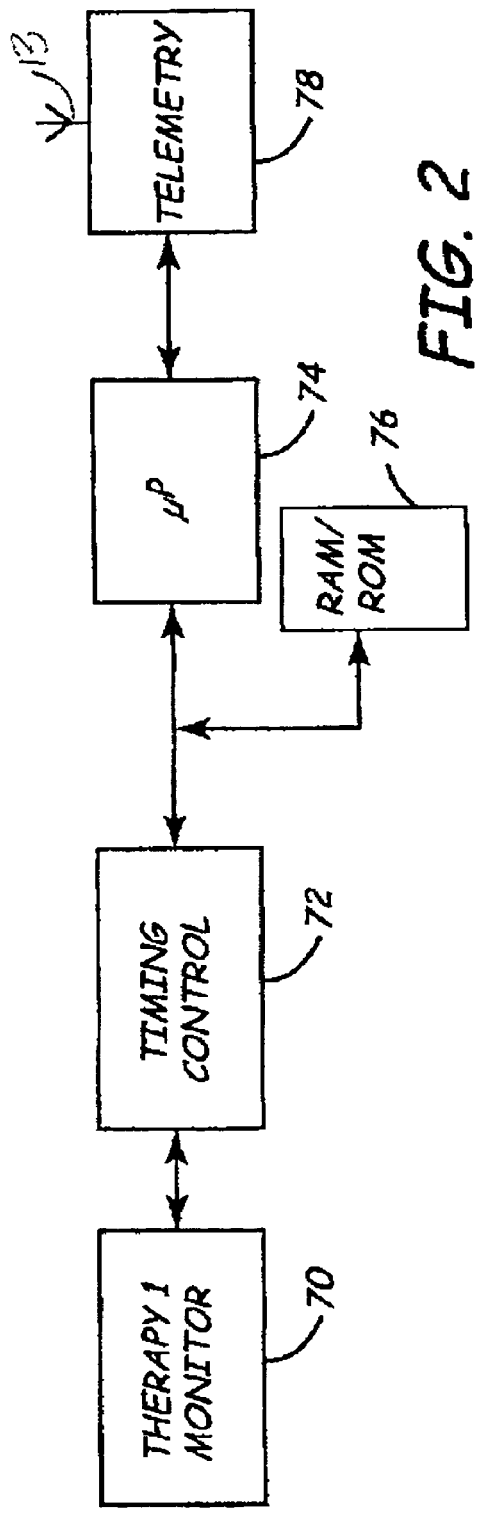
FIG. 2 illustrates typical components of the IMD shown in FIG. 1.

FIG. 2 illustrates typical components of IMD 10 shown in FIG. 1. Specifically, major operative structures common to IMD 10 are represented in a generic format. IMD 10 contains timing and control circuitry 72 and an operating system that may employ microprocessor 74 or a digital state machine for timing, sensing and pacing functions in accordance with a programmed operating mode. IMD 10 also contains therapy/monitor 70 which may include sense amplifiers for detecting cardiac signals, patient activity sensors or other physiologic sensors for sensing the need for cardiac output, and pulse generating output circuits for delivering pacing pulses to at least one heart chamber of heart 16 (see FIG. 1) under control of the operating system in a manner well known in the prior art. The operating system includes memory registers or RAM/ROM 76 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry out on receipt of a retrieval or interrogation instruction. All of these functions and operations are well known in the art, and many are generally employed to store operating commands and data for controlling device operation and for later retrieval to diagnose device function or patient condition.

Programming commands or data are transmitted between IMD 10 RF telemetry antenna 13 and an external RF telemetry antenna 15 associated with EMD 22, as described previously. RF telemetry antenna 13 is coupled to a telemetry transceiver 78 including a telemetry transmitter and telemetry receiver. The telemetry transmitter and telemetry receiver in IMD 10 are coupled to control circuitry and registers operated under the control of microcomputer 74.

Figure 3:
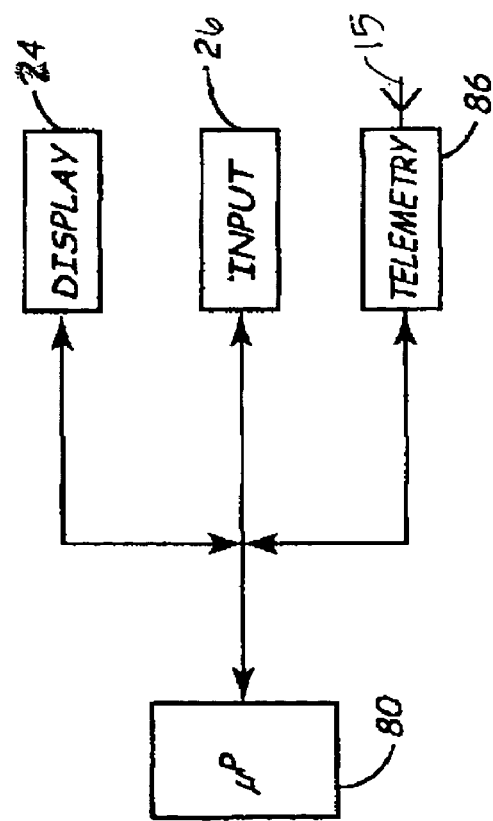
FIG. 3 is a simplified block diagram of major functional components typically included in the EMD shown in FIG. 1.

FIG. 3 is a simplified block diagram of major functional components typically included in an EMD, such as EMD 22 shown in FIG. 1. The external RF telemetry antenna 15 on EMD 22 is coupled to a telemetry transceiver 86, which includes an antenna driver circuit board having a telemetry transmitter and telemetry receiver. The telemetry transmitter and telemetry receiver are coupled to control circuitry and registers operated under the control of microcomputer 80.

EMD 22 may be a personal computer type, microprocessor-based device incorporating a central processing unit 80, which may be, for example, an Intel Pentium microprocessor or the like. A system bus interconnects CPU 80 with a hard disk drive, storing operational programs and data, and with a graphics circuit and an interface controller module. A floppy disk drive or a CD ROM drive may also be coupled to the bus and is accessible via a disk insertion slot within the housing of EMD 22. EMD 22 may include solid-state memory for long-term storage of data.

In order for the physician, patient, or other caregiver or authorized operator to interact with the EMD 22, a keyboard or other user interface input 26 coupled to CPU 80 is optionally provided. However the primary communications mode may be through graphics display screen of the well-known "touch sensitive" type controlled by a graphics circuit. A user of EMD 22 may interact therewith through the use of a stylus, also coupled to a graphics circuit, which is used to point to various locations on screen or display 24 which display menu choices for selection by the user or an alphanumeric keyboard for entering text or numbers and other symbols. Various touch-screen assemblies are known and commercially available. Display 24 and/or the user interface 26 allow a user to enter command signals to initiate transmissions of downlink or uplink telemetry and to initiate and control telemetry sessions once a telemetry link with an implanted device has been established. Other types of user interaction mechanisms and electronics may be implemented such as voice recognition/response systems.

Display screen 24 is also used to display patient related data, menu choices and data entry fields used in entering the data or messages alerting a patient or user to pertinent programming or monitoring conditions. Display screen 24 also displays a variety of screens of telemetered out data or real time data. Display screen 24 may also display uplinked event signals as they are received and thereby serve as a means for enabling the user to timely review IMD operating history and status.

EMD 22 may also include an interface module, which includes a digital circuit, non-isolated analog circuit, and/or isolated analog circuit for coupling peripheral or accessory devices or instruments to EMD 22. The digital circuit enables the interface module to communicate with the interface controller module. For example, EMD 22 may be provided with a strip chart printer or the like coupled to interface controller module so that a hard copy of a patient's ECG, EGM, marker channel of graphics displayed on the display screen can be generated. EMD 22 may be embodied or include features as generally disclosed in U.S. Pat. No. 5,345,362 (Winkler), which is incorporated by reference herein in its entirety.

Figure 4:
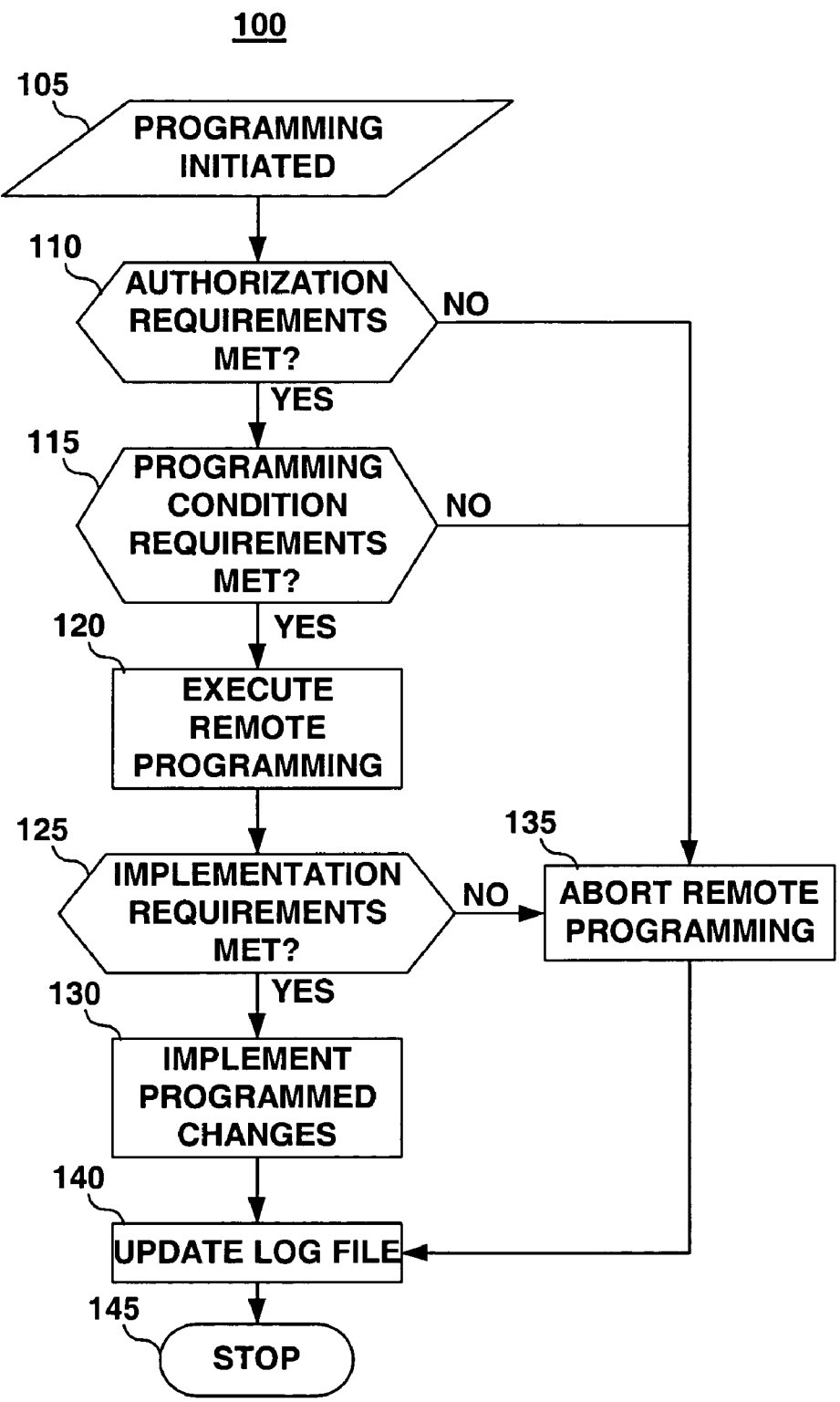
FIG. 4 is a flow chart summarizing aspects of a remote programming method for use with the system shown in FIG. 1 in accordance with the present invention.

FIG. 4 is a flow chart summarizing aspects of a remote programming method 100 for use with the system shown in FIG. 1 in accordance with the present invention. A remote programming session is initiated at step 105. A remote programming session will typically be initiated by a clinician or other user using a centralized programming instrument. Alternatively, a remote programming session may be initiated automatically by a centralized programming instrument, for example in accordance with a predefined prescribed schedule of programming changes. A remote programming session could also be initiated by the remote EMD located in the vicinity of the patient, either spontaneously or at request of an IMD. An EMD may make a request for a programming change to be executed from a centralized programming instrument, automatically or by a clinician.

Decision steps 110, 115, and 125 and step 140 represent various remote programming requirements that may be imposed in a remote programming method to promote patient safety and security. At decision step 110, authorization requirements may be imposed before allowing a remote programming session to commence. Authorization requirements may include authentication of the identity of a user, centralized programming instrument, targeted patient, and/or targeted IMD and may further include encryption/decryption requirements or other security functions. Detailed examples of authorization requirements that may be employed by a remote programming method will be described in conjunction with FIGS. 5A and 5B.

If authorization requirements are met, as determined at step 110, or if none have been defined, remote programming method 100 proceeds to decision step 115 wherein programming condition requirements may be imposed relating to the condition of the targeted patient and/or IMD. Patient-related programming condition requirements may be physiological or logistical requirements. Device-related programming condition requirements may relate to the operating or battery status of the IMD. These and other examples of programming condition requirements will be described in greater detail in conjunction with FIGS. 6A and 6B.

If any defined authorization and/or remote programming condition requirements are unmet, method 100 aborts the remote programming session at step 135. A message may be displayed to a user and/or patient indicating an attempted remote programming session and any unmet requirement. If all defined authorization and/or programming condition requirements are met, method 100 proceeds to step 120 allowing the remote programming session to proceed.

During execution of a remote programming operation, programmable parameters used by the IMD to control device functions may be changed, new operating code may be installed to update or upgrade the operational modes or features of the IMD, or other data may be transferred to the IMD. A remote programming session may also involve transfer of data from an IMD to the centralized programming instrument for evaluation by a clinician prior to or after making remote programming changes. Such data may include physiological data collected and stored by the IMD, device diagnostic data, currently programmed operating parameters, operating code version software modules installed, and the like.

Once remote programming data are entered by a user and transferred from the centralized programming instrument to the targeted IMD via an associated EMD, remote programming method 100 may impose implementation requirements at decision step 125. Implementation requirements define conditions that must be met before the IMD implements the remotely programmed changes executed at step 120. Examples of implementation requirements will be described in greater detail in conjunction with FIGS. 7A and 7B. Generally, implementation requirements may be imposed as an additional safety feature to prevent inadvertently programmed changes to be put to use in controlling IMD functions. Implementation requirements may, for example, require verification of a complete programming transmission and/or verification of pending changes by a user or third party. In case of asynchronous remote programming, implementation requirements may include verification that the IMD status is unchanged since the last time IMD status was acquired by the centralized programming instrument to the time remote programming instructions are transferred to the IMD.

If any defined implementation requirements are unmet, the remote programming session is aborted at step 135 and any pending changes are canceled. If all defined implementation requirements are met, the IMD implements the pending changes at step 130.

Remote programming method 100 may further include step 140 for maintaining a log of remote programming sessions. Sessions that are successfully completed or aborted due to unsatisfied remote programming requirements may be logged to allow remote programming session records to be audited for safety and security issues. A number of parameters may be stored in a log file including any of, but not limited to: the time, date and duration of a remote programming session; user identification; centralized remote programming instrument identification; targeted medical device identification, e.g. device serial number; patient identification; original programmed parameters settings, features, or program version; changed parameters, features or program version; final programmed settings, features, or program version; success or failure of remote programming session and unmet requirements if session failed; and user-entered comments.

A programming log file may also document programming sessions that are performed non-remotely, e.g. during an office visit, such that a complete history of device programming history is available. A programming log file may be stored in the centralized programming instrument or associated system, on a host network server, or in an external or implantable medical device.

The remote monitoring session is then terminated at step 145 after completing the optional remote monitoring session log updates at step 140. Thus, a remote programming method may include any of a variety of safety or security related requirements that must be satisfied for a remote programming operation to be successfully completed. For the sake of illustration, such requirements have been classified generally in FIG. 4 as authorization requirements, programming condition requirements, implementation requirements and maintenance of a programming session log. It is recognized that a remote programming method may include one or more requirements that fall generally into any of these categories or otherwise relate to ensuring safe, secure remote programming of a medical device.

The software code implementing such requirements may be installed on the central programming instrument or associated system, a networked host server, an EMD or IMD, or across these system components. Remote programming requirements may be customized for individual patients or devices. For example, various requirements may be incorporated in a remotely programmable medical device system and be selectively enabled or disabled by a supervising clinician.

Figure 5A:
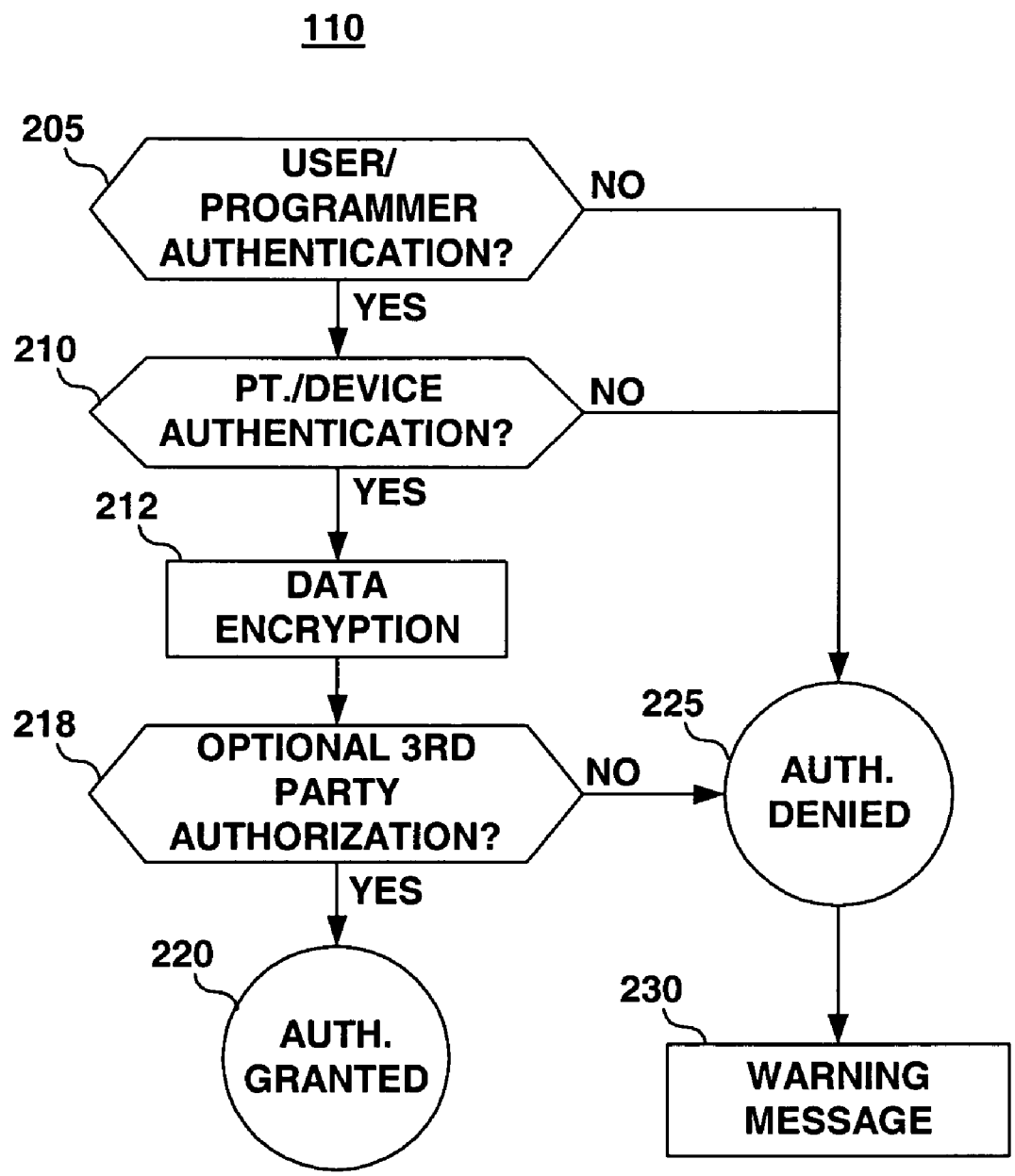
FIG. 5A is a flow chart summarizing steps that may be included in a decision step included in the method of FIG. 4 for verifying that remote programming authorization requirements have been met.

FIG. 5A is a diagram summarizing steps that may be included in decision step 110 of FIG. 4 for verifying that all defined authorization requirements have been met. Step 110 of FIG. 4 is represented in FIG. 5A as a subroutine executed to determine if all authorization requirements are met. Authorization requirements may include authentication requirements relating to the identity of a user attempting to execute a remote programming session or the type of centralized programming instrument being used as indicated at decision step 205.

A variety of user authentication methods may be implemented in conjunction with a remote programming method. User authentication may require a user identification element and associated password or rely on a public key/private key system or a zero-knowledge protocol to allow remote programming access. User authentication may alternatively employ biometric authentication methods such as a retina scan, fingerprint, voice recognition, facial image, and the like, or use of a user carried token, such as a swipe card or SecurID-type timed random number card. User authorization may alternatively require a specific series of commands to be entered by a user on the centralized programming instrument and/or received by a network server to enable remote programming capabilities.

Methods of user authentication will typically be implemented and run on the centralized programming instrument or associated system or on a network server but could also run on a remote EMD or the targeted IMD or a combination of system elements when two-way communication is required. Two-way communication protocols, such as zero-knowledge protocols, may be implemented for user authentication. In a zero-knowledge protocol, the centralized programming instrument may act as the "prover" and a network server, remote EMD or IMD may act as the "verifier" in a protocol designed to prove the mutual identities of the user and the targeted IMD.

User authentication elements may be coded to allow user-specific levels of accessibility to remote programming capabilities. A more highly trained clinician may be authorized to perform a wider range of remote programming operations than a lesser-trained user. Access to remote programming changes that may affect the clinical well being or safety of the patient may thereby be limited to users qualified to supervise such changes.

Other safety features may be implemented in connection with user authentication methods. A user identification element may be "locked" if a maximum number of allowable attempts to enter an associated password is exceeded. A list of valid, authorized identification elements and/or a list of invalid, unauthorized identification elements may be maintained on a server or the centralized programming instrument. Upon user authorization, a message may be displayed on the centralized programming instrument alerting the user of the most recent remote programming session executed under the same user identification element. A warning may be provided to a targeted patient notifying them that an unexpected user has initiated a remote programming session.

Authorization requirements may further include authenticating the targeted patient identification or targeted IMD as indicated by decision step 210 of subroutine 110. One method for authenticating the targeted IMD may simply involve matching the unique IMD serial number with a serial number entered by a user on the centralized programming instrument. Methods for authenticating a targeted patient's identity may involve matching biometric identification elements stored in the memory of the IMD or associated EMD. A facial image, retina scan, fingerprint, voiceprint or other biometric identification element could be stored. Alternative, biometric parameters used for identity matching could be obtained from physiological signals or measurements acquired and stored by the IMD. Such parameters may be derived from EGM signal morphology, pressure, activity, respiration, temperature, heart rate, heart rate variability, lead impedance or inductance measurements, body capacitance measurements or other physiological signals or measurements.

In other embodiments, encryption/decryption schemes may be used to enable remote programming as indicated by step 212. A digital certificate may be used to authenticate a user identity and deliver a digital signature used to verify that a set of remote programming instructions arrived intact. A public/private key scheme may be used wherein a unique private key is stored on an IMD. A corresponding public key is stored on a centralized programming instrument or available from a data file on a network server for all IMDs programmed by that instrument. In one embodiment, a public key may be based on a formula using the IMD model number and/or serial number. A set of remote programming instructions may include a header having a standard instruction defined by the public key. Only remote programming instructions transmitted using the correct public key will decrypt using the private key in the targeted IMD to produce meaningful instructions usable by the IMD. The standard instruction will allow verification that the decryption worked correctly thereby verifying that the correct IMD received the transmitted to communicate with the targeted IMD or EMD would obtain the current pseudorandom number for the targeted IMD and use that number, alone or in combination with another number such as the device serial number, to encrypt the programming instructions. Only instructions encrypted with the correct number will be properly decrypted for use by the IMD.

It is recognized that numerous encryption/decryption schemes may be used to ensure that a set of remote programming instructions are received only by a correctly targeted IMD. Such encryption/decryption methods further ensure patient privacy and can be used to verify complete transmission of a set of remote programming instructions.

Figure 5B:
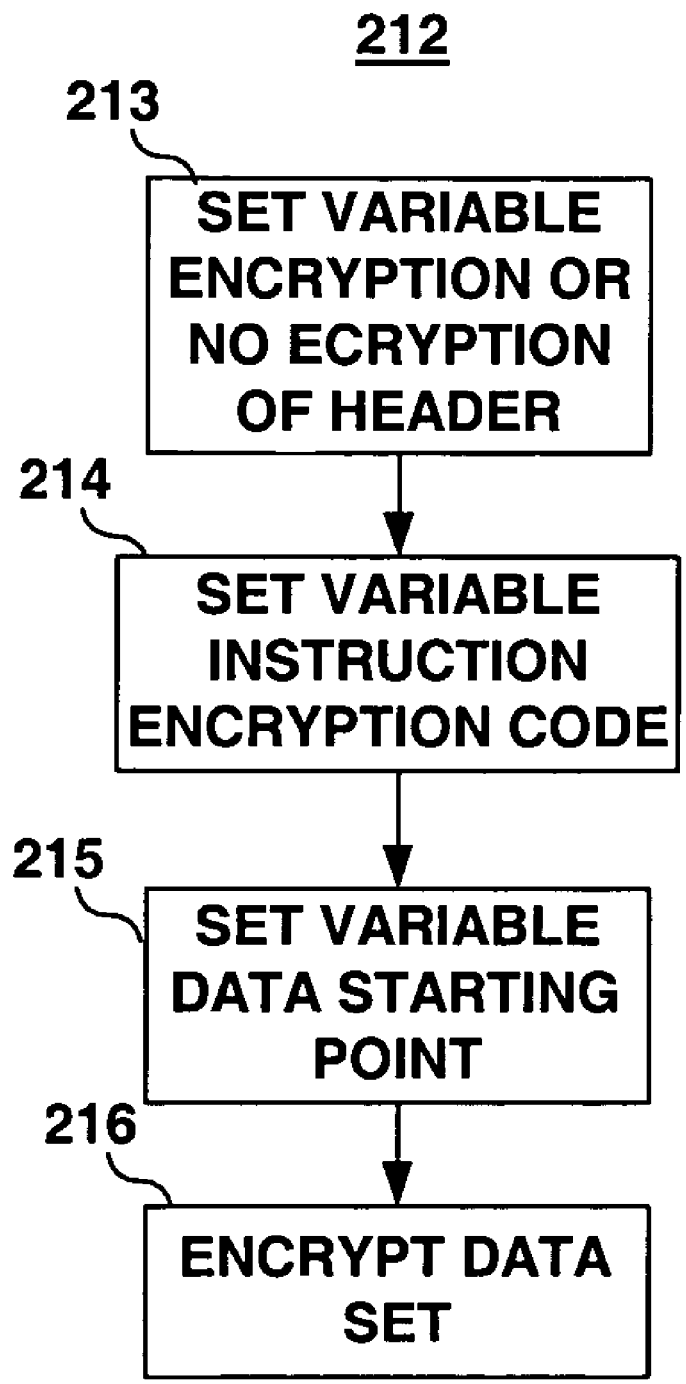
FIG. 5B is a flow chart summarizing steps included in an encryption method that may be included in the method of FIG. 5A to promote secure data transfer.

FIG. 5B summarizes encryption methods that may be included in encryption step 212 of method 200 to promote secure data transfer. At step 213, header encryption methods are selected. Header information, which typically contains the same type of information for each remote programming session, may be left unencrypted so as to prevent easy encryption code deciphering. Alternatively the header may be encrypted using variable encryption code. If the header is to be encrypted, header encryption codes may be varied at specified intervals of time or following each remote programming session to reduce the likelihood of unauthorized decryption.

At step 214, a variable encryption code used for encrypting the remainder of the remote programming instructions may be set. The variable code used for encryption of the instruction set may be the same or different than variable encryption code used for encrypting the header, when it is encrypted. At step 215, the data starting point for the transferred instruction set is selected. The remote programming data pattern may be varied, e.g., by providing a variable starting point in the data, to reduce the likelihood of unauthorized decryption. At step 216, the data set is encrypted according to the selected header and instruction set encryption methods and selected data starting point.

After data encryption methods have been performed, method 200 of FIG. 5A may proceed to step 218. At decision step 218, an optional third party authorization may be required before granting remote programming authorization at step 220. If a patient is enrolled in a clinical study, for example, third party approval may be required to allow remote programming changes to ensure such changes are within study requirements. In other cases, programming instructions entered by an authorized user may require approval of a more qualified clinician or panel before being transmitted to a targeted IMD.

Any required user/programmer authentication, patient/device authentication, encryption, and optional third party authorizations must be acquired before remote programming authorization is granted at step 220. If any required authentication or third party authorization is not obtained, authorization is denied at step 225. A warning message may be displayed at step 230 to alert the attempting user or targeted patient of the denied authorization and the reason for denying authorization.

As described previously, remote programming requirements may additionally include programming conditions under which remote programming is allowed to take place. Decision step 115 of remote programming method 100 shown in FIG. 4 is represented as a subroutine in FIG. 6A for determining if programming condition requirements are met.

Subroutine 115 may include condition requirements relating to a number of aspects of the remotely programmable medical device system and targeted patient. Examples of programming condition requirements that may be applied are described herein according to a number of general categories for the sake of illustration. General categories of programming condition requirements may include temporal conditions (step 250), physiological or patient-related conditions (step 255), logistical conditions (step 260), and device-related conditions (step 265).

At step 250, subroutine 115 determines if temporal programming condition requirements are met. A variety of time-related remote programming conditions may be set based, for example, on time of day, time since implantation of the IMD, time since a previous remote programming session, time since a therapy was delivered, or other time-related conditions. Temporal conditions may also relate to the transmission time of the remote programming instructions. A limitation based on the latency present within the communication system used may be imposed to prevent remote programming operations outside of a defined window of time after initiating a transmission. A time-out feature within the EMD or IMD may prevent or abort programming changes if a complete set of instructions is not received within a specified period of time following session initiation. Other time-related conditions may relate to the programming mode, i.e., real-time or asynchronous programming. Remotely programmable parameters or parameter ranges may be limited based on the programming mode or other temporal conditions.

At decision step 255, subroutine 115 determines if physiological or patient-related conditions for allowing remote programming are met. Physiological conditions may be based on current physiological sensor signals or physiological data stored by the IMD or another medical device. For example, remote programming may be limited to occur during a specified level of patient activity or posture as indicated by an activity sensor and/or position sensor. Programming may be limited to when a patient is resting in a prone position, when a patient is upright and active, or other activity/position criteria. Remote programming may be limited to periods of time when a patient is determined to be in normal sinus rhythm or when experiencing an adverse arrhythmia. For example, a patient may be experiencing an arrhythmia but arrhythmia detection or therapy features may be disabled in an implantable cardioverter/defibrillator. Arrhythmia detection or therapies could be enabled via remote programming. Other physiological conditions may be defined based on respiration, blood oxygen saturation, blood glucose level, blood pressure or other hemodynamic metrics. It is recognized that any of a number of physiological conditions may be defined based on sensing physiological signals.

Physiological conditions may be ascertained using a separate implantable or external medical device other than the IMD targeted for remote programming. Physiological conditions may be used to allow or prevent remote programming or may be used to set limitations on the parameters or ranges of parameter values that are programmable. In one example, if a patient is experiencing atrial fibrillation or flutter, remote programming may be limited to operations that maintain automatic pacing mode switching.

Another patient-related programming condition may require that the patient be aware that remote programming operations are going to occur. A message alerting the patient that an authorized user is initiating a programming session may be displayed or another alert signal generated. A patient response may then be required affirming that a remote programming session may proceed. Such a response may include any of: "waking up" the implantable device by the patient so that it is ready to receive telemetry, e.g. by swiping a magnet over the device; entering a code or voice message into the EMD, tapping a certain pattern detectable by a motion sensor in the IMD on the patient's skin above the IMD, or placing a telephone call to the authorized user. It is recognized that a large range of mechanisms are possible to assure that the patient is aware of the programming session.

At decision step 260, subroutine 115 determines if any logistical programming condition requirements are met. Logistical requirements may relate to the location of the patient at the time of remote programming, e.g. the patient's proximity to a clinical center or emergency responders, another person in the presence of the patient at the time of remote programming, or the availability of emergency medical or monitoring equipment such as having ECG electrodes, an external defibrillator or other instrumentation available or attached to the patient. The patient may be required to hold a "disconnect" switch in which case, if a patient experiences an adverse affect and releases the "disconnect" switch, remote programming operations are aborted and prior IMD programming is restored. Confirmation of a patient's location may be made using Global Positioning System (GPS) technology. Alternatively, patient location and/or instrumentation requirements may be confirmed manually by the patient or another person.

Other logistical requirements may relate to communication links established between the centralized programming instrument and the remote EMD and/or communication connections between the patient and the clinician or other user performing the programming. For example, minimum telemetry signal quality, minimum transmission speed or a maximum bit error rate (BER) may be set at various points on the remote programming system. Alternatively, a maximum response time for the remote EMD or IMD to respond to a programming request may be specified. An active telephone or voice communication connection may be required between the patient and the clinician or other user performing the programming prior to and/or during remote programming.

At decision step 265, subroutine 115 verifies that any device-related programming condition requirements are met. Remote programming functions may be limited according to the type of centralized programming instrument being used, the type of EMD being used, the telemetry scheme employed between an EMD and targeted IMD, or other device-related specifications. Device-related programming conditions may also specify the status of currently programmed IMD settings, number of prior programming sessions in a clinical environment, device diagnostics, battery charge, time since delivered therapy, activation or "wake-up" method used to enable IMD telemetry circuitry to receive data, or other IMD status conditions.

An IMD may be shipped with a factory setting that prevents remote programming, requiring a clinician to enable the IMD for this capability. A tiered approach may be applied wherein the first remote programming session would have greater limitations on authorized programming functions than subsequent remote programming sessions.

In a patient with multiple implantable medical devices, a communication scheme between the IMDs may enable, prevent or limit remote programming of one IMD based on feedback or information received from another IMD. In systems including one or more IMDs, a self-diagnostic check or system test may be required prior to authorizing remote programming. Each element of the overall remote programming and medical device system may determine the readiness of elements or the system as a whole for remote programming. Based on such self-diagnostic checks or system tests, each element of the system may be enabled to cancel or authorize a remote programming system. A cancellation by any given element may override remote programming authorized by another system element.

If any specified programming condition requirements are unmet, subroutine 115 determines a failure to meet programming conditions at step 275. A warning message may be issued at step 280 to alert a user and/or patient of the failed remote programming condition requirements and may make recommendations to satisfy programming condition requirements. If all selected temporal, patient-related or physiological, logistical and device-related programming condition requirements are met at decision steps 250 through 265, subroutine 115 concludes remote programming conditions are satisfied at step 270, and remote programming operations may proceed as described previously in conjunction with FIG. 4.

Figure 6A:
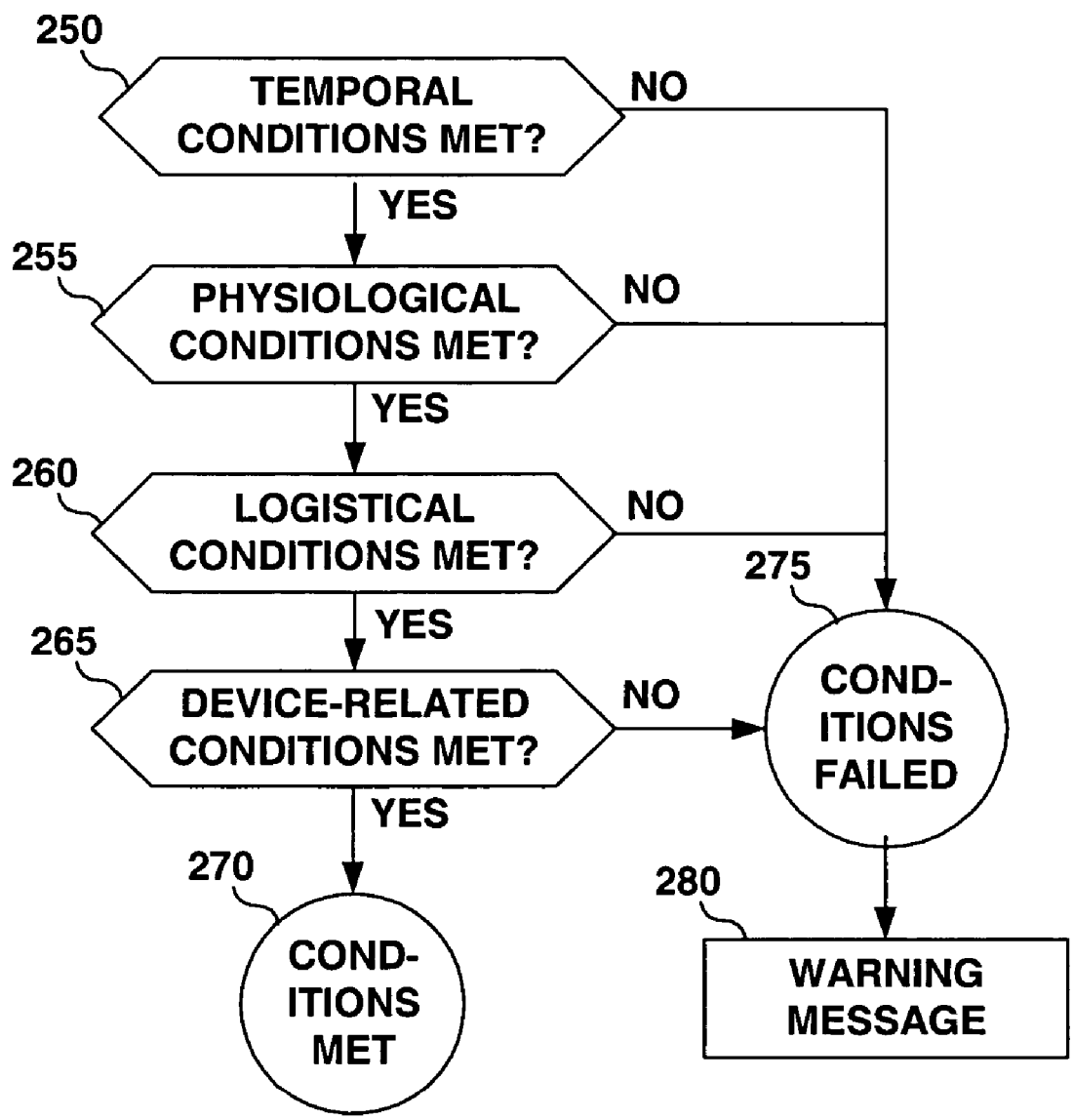
FIG. 6A is a flow chart summarizing steps that may be included in a decision step included in the method of FIG. 4 for determining if remote programming condition requirements are met.
Figure 6B:
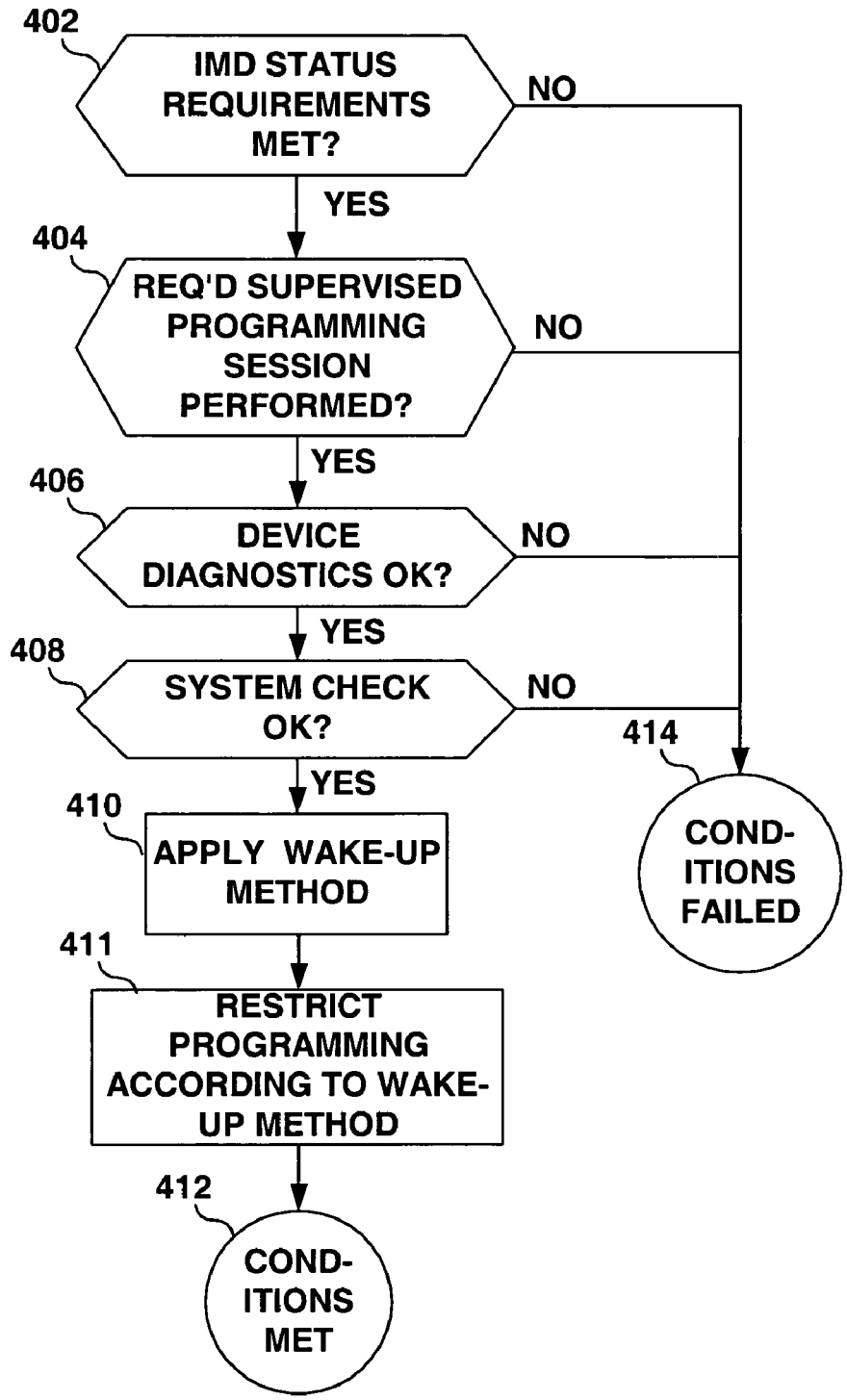
FIG. 6B is a flow chart summarizing device-related programming condition requirements that may be imposed.

FIG. 6B is a flow chart summarizing a method for verifying device-related programming condition requirements that may be imposed at step 285 of subroutine 115 shown in FIG. 6A. At step decision step 402, the state of the IMD programmed parameters and/or therapy delivery history may be examined to verify that the status of programmed values or therapy history is not contrary to any device-related condition requirements at the time of the remote programming session. An interrogation of IMD settings may be required to verify that remote programming changes would not conflict with current IMD status, causing an undesired or unsafe status.

In some cases, remote programming may be performed asynchronously, i.e. a delay may exist between sending programming instructions and implementation of instructions by the IMD. Therefore, verification of IMD status requirements may need to be performed both at the time of transferring remote programming instructions as shown by step 402 and at a later time, prior to implementing programming instructions. A method for verifying that all or at least critical aspects of IMD status remain unchanged prior to implementation of asynchronous remote programming changes will be described in detail below with regard to implementation requirements.

At decision step 404, none, one or more prior programming sessions under direct supervision of a clinician or other authorized personnel may be required before allowing a remote programming session to be performed. During a direct supervised programming session, the clinician may program the IMD to be enabled for future remote programming sessions. Alternatively, a log of programming sessions may be updated and once the pre-requisite number of supervised programming sessions has been met, the IMD may be automatically enabled for remote programming.

At decision step 406, results of device diagnostic checks may be examined and compared to device-related programming condition requirements. Device diagnostic tests may be related to pacing threshold tests, lead impedance tests, battery status updates, or other tests designed to evaluate device performance. At decision step 408, a system check may be performed in patients having multiple implantable devices or for verifying that the expected types of remote programming instrument, EMD, and telemetry systems being used meet any specified programming condition requirements.

At step 410, a wake-up method for activating the IMD telemetry circuitry such that it is ready to receive a telemetry downlink from the EMD is applied. The wake-up method applied may be specified such that only particular wake-up methods may be used to enable receipt of remote programming instructions. The wake-up method used may be selected based on the level of security desired. In a less secure setting, the wake-up method may use a distance activation method such as an RF link or other wireless signal method without requiring intervention by the patient or another person in the presence of the patient. The programmable parameters and parameter ranges or values may be restricted based on the wake-up method used as indicated by step 411. In less secure settings using distance activation, greater programming restrictions may be imposed.

To ensure greater security, a proximal wake-up method may be required which generally requires intervention by the patient or another person in the presence of the patient. Examples of proximal wake-up methods include: finger-tapping on the device, application of a sub-audible or audible vibrating tone using a vibrating device, a digital pulse or tapping applied to the skin over the IMD using a tapping device, a magnet swipe, and a manually activated RF or other wireless signal from an EMD or other transmitting device to the IMD. Fewer or no restrictions on remote programming operations may be imposed at step 411 when proximal wake-up methods are used rather than distance activation.

If all device-related requirements are satisfied as determined at decision steps 402 through 408 and the required wake-up method has been applied at step 410, the device-related programming conditions may be concluded to be satisfied at step 412. If any requirements are unmet, the device-related programming conditions are concluded to be unsatisfied at step 414.

After fulfilling any authorization and/or programming condition requirements, a remote programming data transmission may be performed. However, certain implementation requirements may need to be satisfied before pending remote programming changes are accepted and put to use by the IMD in controlling device operations. Implementation requirements may be directed toward ensuring that a remote programming transmission was received completely and correctly before implementing programming changes. If unintended or incomplete programming changes are implemented, medical device function may be altered in a way that adversely affects the well being of the patient. Therefore implementation requirements may be specified as a safety feature for ensuring only correct and intended programming changes will be made.

Implementation requirements may also be directed toward ensuring that no changes to the state of the IMD have occurred between the time that a set of remote programming instructions were sent by a user and the time that the instructions are actually transferred to an IMD. Transfer of remote programming instructions to an IMD will occur after some time delay following transmission from the remote programming instrument. This delay may be only a few seconds or minutes when the IMD is enabled and ready for receiving downlink telemetry from an associated EMD. However, if the IMD is not enabled or not within telemetric communication of the EMD at the time of remote programming transmission, an unknown time delay of hours or even days or weeks may occur before instructions are transferred to the IMD. During this time delay, the IMD state may change. The patient may visit a clinic and undergo a supervised programming session, or the history of therapy delivery, arrhythmia episode detection or other physiologic event detection may have changed since the remote programming instructions were initially sent by a clinician or user. Such IMD state changes may be of clinical importance with regard to the intended programming changes, making the programming changes inappropriate or undesired.

Figure 7A:
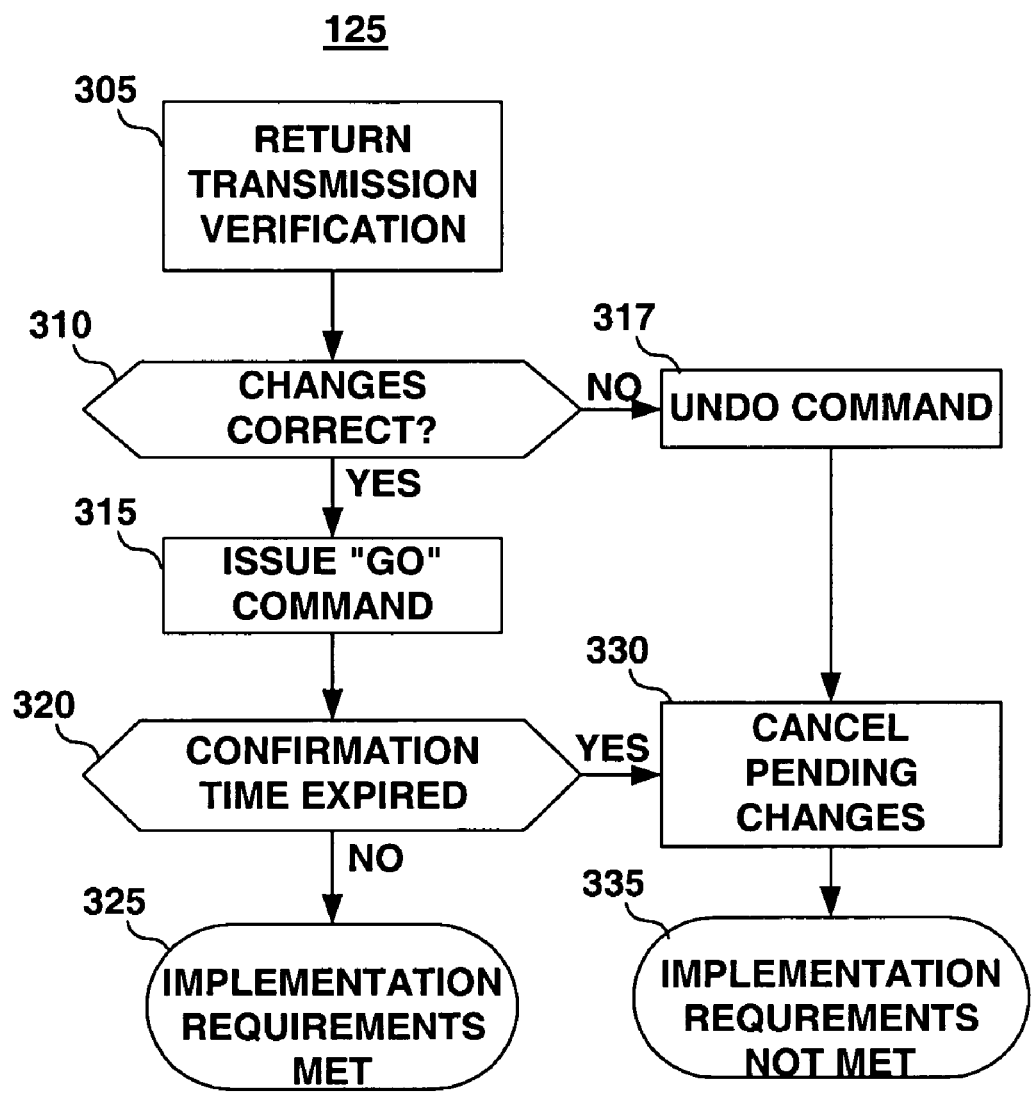
FIG. 7A is a flow chart summarizing steps that may be included in a decision step included in the method of FIG. 4 for determining if remote programming implementation requirements are met.

Decision step 125 shown in FIG. 4 for verifying that implementation requirements have been met is shown in FIG. 7A as a subroutine. Specifically, steps that may be included in one method for verifying that implementation requirements are satisfied are summarized. At step 305, a return transmission from the programmed IMD to the centralized programming instrument is issued after the remote programming instructions have been received. The return transmission may confirm complete transmission of the remote programming data. Complete transmission may be verified using the encryption/decryption methods or digital certificates described previously for verifying that an entire transmission is received intact. Verification of complete transmission may be automatic by the medical device after which the device may implement the changes and issue a return transmission indicating complete transmission. Implementation of changes may then occur automatically.

Alternatively, a return transmission issued at step 305 may list the programming changes received. The changes could be manually or automatically compared to the original programming instructions. If the changes do not match the original programming instructions, an "undo" command may be issued automatically or manually at step 317. The pending changes would be canceled at step 330, and the previously programmed settings and code would be maintained. Subroutine 125 would conclude at step 335 with the decision that implementation requirements have not been met.

If the programming changes do match the original programming instructions, as determined at decision step 310, a "go" command may be issued at step 315, manually or automatically, authorizing implementation of the changes. At decision step 320, an optional confirmation time limit may be applied during which a "go" command confirming correct programming changes must be received in order for implementation of programming changes to take place. This additional safety feature would allow pending changes to be cancelled at step 330 if a specified confirmation time expires before receipt of a "go" command. Subroutine 125 would then conclude at step 335 with the decision that implementation requirements are not met.

If complete transmission and correct changes are verified within any specified time limit, subroutine 125 concludes at step 325 with the decision that implementation requirements have been met. Remote programming method 100 may then proceed as described previously, by either aborting the remote programming session or implementing the programmed changes according to whether the implementation requirements were met.

Figure 7B:
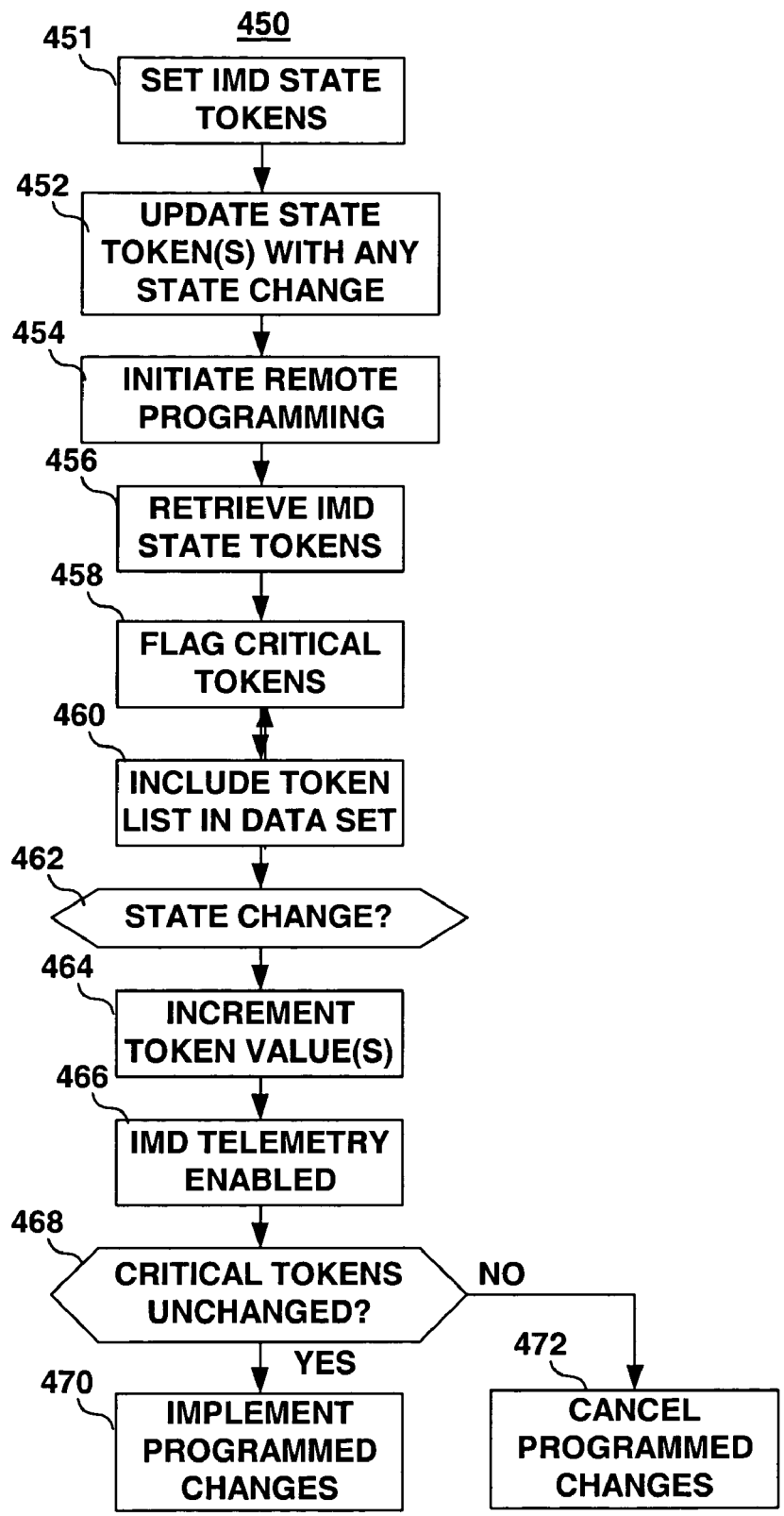
FIG. 7B is a flow chart summarizing steps included in a method for verifying IMD state requirements prior to allowing a remote programming session to proceed.

FIG. 7B is a flow chart summarizing steps included in a method for verifying IMD state requirements prior to allowing a remote programming changes to be implemented by the IMD. Method 450 provides a way of verifying that the IMD state, or at least critical aspects of the IMD state relevant to intended remote programming changes, has not changed since a remote programming instruction set was transmitted. Applying remotely programmed changes against an altered IMD context could leave the IMD in an unsafe state or could unknowingly remove previous programming changes. The method of FIG. 7B may be performed alone or in addition to the implementation requirements summarized in FIG. 7A.

At step 451, a number of IMD state tokens, which may be stored within the IMD, are set to initial values. A state token may represent the state of an IMD operating parameter or a set of operating parameters such as cardiac pacing parameters, therapy delivery parameters, arrhythmia detection parameters or the like. A state token may also represent the state of a device diagnostic or set of device diagnostic parameters, the state of one or more patient or clinician alert parameters, the state of therapies delivered by the IMD, the state of detected arrhythmia episodes or other physiological events, or the like. A token may be implemented as a time-date stamp, a counter, or some other non-repeating deterministic or random sequence. The token value is the time-date stamp value or other value in a series of non-repeating values at the time the token was set.

If any of the IMD state parameters that are being tracked by a state token change, the token value(s) are updated at step 452. A time-date token value is updated by changing the token value to the date that the IMD state change occurred. In other implementations of the state token, the token value is advanced to the next value in a non-repeating sequence. A non-repeating sequence of values may be non-repeating over some finite bound if an upper bound can be established corresponding to the longest time delay anticipated or allowed between sending remote programming instructions and downlinking them to the IMD.

A remote programming session may be initiated at step 454. When the remote programming session is initiated, the IMD state token values are retrieved from the IMD at step 456, if communication with the IMD is available. If communication with the IMD is not available, i.e. programming is being performed asynchronously, the IMD state token values most recently acquired by the centralized programming instrument are used. IMD state token values may also be stored in an associated EMD and updated periodically or whenever the IMD and EMD are within communication range. As such, the most recent state token values stored by the EMD may be retrieved by the central programming instrument upon establishing a communication link with the EMD, even if communication with the IMD is unavailable at the time of the remote programming session.

The clinician or user may flag critical tokens that should remain unchanged before enabling implementation of remote programming instructions by the IMD. Depending on the programming changes being made, some aspects of the IMD state may be critical and some not with regard to the intended programming changes. Therefore, changes in some state token values may be acceptable in implementing remote programming changes and others may make remote programming changes inappropriate or unsafe. Flagging of critical tokens may alternatively or additionally be performed automatically by the remote programming system. Interlocks may be created within remote programming software that prevent implementation of remote programming changes to particular IMD operating parameters if certain state tokens have changes since the remote programming session was initiated. Such interlocks may be implemented in the centralized programming instrument, a networked host server, the IMD or the associated EMD.

When the remote programming data is transferred to the associated EMD, a state token list is included in the data set representing the state token values at the time of transmission, as indicated by step 460. Meanwhile, the IMD state continues to be monitored such that if any IMD state changes occur, as determined at decision step 462, the token values continue to be updated at step 464. Once the IMD telemetry system is enabled to receive the remote programming data at step 466, which may occur after some time delay following transmission of the remote programming instructions to the EMD, a verification is made at decision step 468 that any critical tokens are unchanged by comparing the current token values to the token values provided with the transferred programming data. If any critical token values have changed, the implementation requirements are unmet, and pending remotely programmed changes are canceled at step 472. If critical token values are unchanged, implementation requirements are met, and remotely programming instructions are implemented by the IMD at step 470.

Thus, a medical device remote programming method has been described including remote programming requirements for advantageously promoting patient safety and privacy during programming sessions performed across communication networks. It is recognized that one of skill in the art may conceive of a variety of remote programming requirements and variations of implementing such requirements. The various examples of authorization, programming condition, and implementation requirements and a programming session log file described herein are intended to illustrate how various aspects of the present invention may be put to practice in a remote programming system and method. The detailed embodiments described herein, therefore, are intended to be exemplary and not limiting with regard to the following claims.

What is claimed is:

1. A method, comprising:
   initiating a remote programming session using a centralized programming instrument capable of communicating with a remote medical device;
   verifying that one or more predetermined remote programming requirements are satisfied;
   entering remote programming instructions at the centralized programming instrument;
   transmitting the remote programming instructions from the centralized programming instrument to the remote medical device; and
   implementing remote programming instructions in the remote medical device if the one or more remote programming requirements are satisfied;
   wherein verifying the one or more remote programming requirements are satisfied comprises verifying a remote medical device status has not changed between a time the remote programming instructions are entered and a time the remote programming instructions are received by the remote medical device.

2. The method according to claim 1 further including updating a programming log file upon implementing the remote programming session.

3. The method of claim 1 wherein the remote programming requirements includes one or more authorization requirements, which if satisfied, allow the remote programming session to proceed.

4. The method of claim 3 further including verifying a user identification.

5. The method of claim 3 further including verifying the central programming instrument identification.

6. The method of claim 3 further including verifying a targeted patient identification.

7. The method of claim 3 further including verifying the remote medical device identification.

8. The method of claim 3 further including verifying a third party authorization.

9. The method of claim 1 further including limiting remote programming capabilities based on the remote programming requirements that are satisfied.

10. The method of claim 1 further including generating a notification signal to a patient having the medical device of an attempt to verify a remote programming requirement.

11. The method of claim 1 further including encrypting and decrypting remote programming instructions.

12. The method of claim 11 wherein the method for encrypting and decrypting the remote programming instructions includes a method selected from the group of: a public and private key system; a digital certificate or signature; an unencrypted data header; variable encryption code; a variable data starting point.

13. The method of claim 1 wherein the remote programming requirements include one or more programming condition requirements, which when satisfied allow a remote programming instruction set to be transferred to the remote medical device.

14. The method of claim 13 wherein the programming condition requirement is a temporal condition.

15. The method of claim 1 further comprising aborting the remote programming session if one or more of the remote programming requirements is not satisfied.

16. The method of claim 13 wherein the programming condition requirement is a patient condition.

17. The method of claim 13 wherein the programming condition is a logistical condition.

18. The method of claim 13 wherein the programming condition is a medical device condition.

19. The method of claim 1 wherein the remote programming requirements include one or more implementation requirements which, when satisfied, allow a remote programming instruction set to be implemented by the medical device.

20. The method of claim 19, further including verifying a complete transmission of the remote programming instruction set from the centralized programming instrument to the remote medical device.

21. The method of claim 19, further including verifying the remote programming instruction set received by the medical device matches the remote programming instruction set transferred from the centralized programming instrument.

22. The method of claim 19, further including verifying a remote medical device status has not changed between the time the remote programming instructions are entered in the centralized programming instrument and time the remote programming instructions are transferred to the remote medical device.

23. The method of claim 1 wherein the one or more remote programming requirements further comprise requiring the patient affirm that a remote programming session may proceed.

24. The method of claim 1 wherein verifying the remote medical device status has not changed comprises verifying the status has not changed between a time the remote programming instructions are transmitted from the centralized programming instrument and a time the remote programming instructions are received by the remote medical device.

25. The method of claim 1, wherein verifying the remote medical device status has not changed comprises:
 setting a state token value to an initial value of a non-repeating sequence of values, the state token corresponding to a set of IMD parameters;
 updating the state token value to a next value of the non-repeating sequence of values in response to a change in an IMD parameter included in the set of IMD parameters;
 retrieving a most recent state token value upon initiating the remote programming session;
 transmitting the most recent state token value with the remote programming instructions from the centralized programming instrument to the remote medical device; and
 comparing the most recent state token value to a current state token value.

26. The method of claim 25 wherein the non-repeating sequence of values is a time-date stamp.

27. The method of claim 25 wherein the non-repeating sequence of values is a random sequence.

28. The method of claim 25 wherein the non-repeating sequence of values is non-repeating over a finite bound corresponding to a maximum expected time between transmitting remote programming instructions and receiving remote programming instructions.

29. The method of claim 25 wherein the remote medical device is an implantable medical device and transmitting the remote programming instructions comprises transmitting the data to a remote external medical device capable of communicating with the implantable medical device and further transmitting the remote programming instructions from the external medical device to the implantable medical device,
 the remote external medical device receiving the updated state token value whenever the implantable medical device and the external medical device are in communication.

30. The method of claim 29 wherein a time delay occurs between transmitting from the centralized programming instrument to the external medical device and transmitting from the external medical device to the implantable medical device.

31. The method of claim 25 further comprising identifying critical state tokens and non-critical state tokens and wherein implementing remote programming instructions comprises enabling implementation of remote programming instructions when non-critical state tokens have changed and critical state tokens have not changed.

32. The method of claim 14 wherein the temporal condition requires a time delay before implementation of the remote programming instructions.

* * * * *